United States Patent [19]

Illingsworth, deceased

[11] E Re. 29,930

[45] Reissued Mar. 13, 1979

[54] DIRECT-POSITIVE SILVER HALIDE EMULSION FOGGED WITH LOW LEVELS OF REDUCTION AND GOLD FOGGING AGENTS

[75] Inventor: Bernard D. Illingsworth, deceased, late of Rochester, N.Y.

[73] Assignee: Eastman Kodak Company, Rochester, N.Y.

[21] Appl. No.: 849,374

[22] Filed: Nov. 7, 1977

Related U.S. Patent Documents

Reissue of:

[64] Patent No.: 3,501,307
Issued: Mar. 17, 1970
Appl. No.: 619,936
Filed: Mar. 2, 1967

U.S. Applications:

[63] Continuation-in-part of Ser. No. 533,448, Mar. 11, 1966, abandoned.

[51] Int. Cl.[2] ..... G03C 1/36

[52] U.S. Cl. ..... 96/100 N; 96/107; 96/108; 96/101; 96/120

[58] Field of Search ..... 96/108, 107, 101, 64, 96/100, 120

[56] References Cited

FOREIGN PATENT DOCUMENTS 723019 2/1955 United Kingdom ..... 96/108

*Primary Examiner*—Won H. Louie, Jr.
*Attorney, Agent, or Firm*—Carl O. Thomas

[57] ABSTRACT

Very high speed direct-positive photographic emulsions comprising silver halide grains fogged with both reduction and gold fogging agents are described. For some applications other fogging agents, e.g. compounds of metals more electropositive than silver, can be substituted for the gold fogging agent. Photographic elements employing such emulsions and processes for preparing them are also disclosed.

49 Claims, No Drawings

DIRECT-POSITIVE SILVER HALIDE EMULSION FOGGED WITH LOW LEVELS OF REDUCTION AND GOLD FOGGING AGENTS

Matter enclosed in heavy brackets [ ] appears in the original patent but forms no part of this reissue specification; matter printed in italics indicates the additions made by reissue.

This application *is a reissue of U.S. Patent 3,501,307 based on U.S. application Ser. No. 619,936, filed Mar. 2, 1967 which in turn* is a continuation-in-part of Illingsworth U.S. application Ser. No. 533,448, filed Mar. 11, 1966 and entitled "Photographic Materials."

This invention relates to photographic materials, their preparation and use. In one of its aspects, this invention relates to direct-positive photographic emulsions and elements comprising fogged silver halide grains and a compound which accepts electrons. In another of its aspects, this invention relates to direct-positive photographic silver halide emulsions and elements comprising reduction and gold fogged silver halide grains which exhibit exceptional photographic speed.

It is known that direct-positive images can be obtained with certain types of photographic silver halide reversal emulsions. As shown in British Patent 723,019, published Feb. 2, 1955, one photographic emulsion of this type is a photographic emulsion comprising an electron trapping compound and silver halide grains which are fogged using a combination of a reducing agent with a gold compound or a compound of a metal more electropositive than silver such as, for example, palladium or platinum. However, in the past, the use of such a combination of fogging agents has resulted in direct-positive photographic silver halide emulsions which exhibit only low photographic speed, for example, photographic speed comparable to that obtained with the customary silver halide emulsions used in enlarging papers and the like. It would, of course, be very desirable to have available, direct-positive photographic silver halide emulsions which comprise reduction and gold fogged silver halide grains and which also exhibit increased photographic speed in comparison to prior art materials.

Accordingly, it is an object of this invention to provide direct-positive photographic emulsions exhibiting good photographic speed.

Another object of this invention is to provide a means for obtaining fogged direct-positive photographic silver halide emulsions and elements which comprise silver halide grains having unique properties.

Still another object of this invention is to provide a means for obtaining fogged direct-positive photographic silver halide emulsions and elements comprising electron trapping compounds such as cyanine dyes.

Still another object of this invention is to provide a means for obtaining an improved photographic reversal emulsion by combining a low level of reduction fogging with a low level of gold fogging of photographic silver halide grains.

Other objects and advantages of this invention will become apparent from an examination of the specification and claims which follow.

The above and other objects of this invention are obtained with fogged silver halide grains characterized by a rapid loss of fog upon bleaching in a chemical bleach and the use of such grains in photographic emulsions, particularly direct-positive photographic emulsions comprising a compound which accepts electrons. The rapid fog loss which characterizes these silver halide grains can be illustrated by comparing (1) the density of processed direct-positive photographic emulsions comprising the fogged silver halide grains which are bleached with (2) identical processed emulsions which are not bleached. The direct-positive photographic emulsions comprising the aforesaid grains can be obtained by fogging photographic silver halide emulsions with a reduction fogging agent in combination with a gold fogging agent at low concentrations.

One embodiment of this invention relates to a direct-positive photographic emulsion which comprises fogged silver halide grains and a compound which accepts electrons, said grains being such that a test portion thereof, when coated as a photographic silver halide emulsion on a support to give a maximum density of a least about one upon processing for six minutes at about 68° F. in Kodak DK-50 developer, has a maximum density which is at least about 30% greater than the maximum density of an identical coated test portion which is processed for six minutes at about 68° F. in Kodak DK-50 developer after being bleached for about 10 minutes at about 68° F. in a bleach composition of:

Potassium cyanide—50 mg.
Acetic acid (glacial)—3.47 cc.
Sodium acetate—11.49 g.
Potassium bromide—119 mg.
Water to 1 liter.

Another embodiment of this invention relates to a photographic element comprising a support and at least one photographic silver halide layer which comprises fogged silver halide grains and a compound which accepts electrons, said grains being such that a test portion thereof, when coated as a photographic silver halide emulsion on a support to give a maximum density of at least about one upon processing for six minutes at about 68° F. in Kodak DK-50 developer, has a maximum density which is at least about 30% greater than the maximum density of an identical coated test portion which is processed for six minutes at about 68° F. in Kodak DK-50 developer after being bleached for about 10 minutes at about 68° F. in a bleach composition of:

Potassium cyanide—50 mg.
Acetic acid (glacial)—3.47 cc.
Sodium acetate—11.49 g.
Potassium bromide—119 mg.
Distilled water to 1 liter.

Another embodiment of this invention relates to a process which comprises contacting silver halide grains with about 0.001 to about 0.06 milliequivalent per mole of silver halide of a reduction fogging agent and about 0.001 to about 0.01 millimole per mole of silver halide of a gold fogging agent at a temperature in the range of about 40° to about 100° C., the ratio of gold fogging agent to reduction fogging agent being in the range of about 1:3 to about 20:1.

The silver halide grains disclosed herein can be fogged with a combination of a reduction fogging agent and a gold fogging agent. In order to obtain fogged silver halide grains which are characterized by a rapid loss of fog upon bleaching, as disclosed herein, it is necessary to employ a very low concentration of reduction fogging agent. It is known that one equivalent weight of a reducing agent will reduce one equivalent weight of silver halide to siver. In practicing this invention, much less than one equivalent weight of the reduction fogging agent is employed. Thus, less than about 0.06 milliequivalent of reduction fogging agent per mole of silver halide is employed in fogging the silver halide grains. Generally, about 0.0005 to about 0.06, preferably about 0.001 to about 0.03 milliequivalent of reduction fogging agent per mole of silver halide is employed in fogging the silver halide grains in the practice of this invention. Prior art procedures employing a combination of reduction and gold fogging agents have employed concentration of the fogging agents substantially in excess of those employed herein and have obtained only very low photographic speeds. A preferred reduction fogging agent employed in the practice of this invention is thiourea dioxide which is generally employed at a concentration in the range of about 0.05 to about 3, preferably about 0.1 to about 2 milligrams per mole of silver halide or about 0.0005 to about 0.03 millimole per mole of silver halide. Stannous chloride is another suitable reduction fogging agent which can be used in practicing this invention and can be used in concentrations in the range of about 0.05 to about 3 milligrams of stannous chloride per mole of silver halide. When higher concentrations of the reduction fogging agent, e.g., thiourea dioxide or stannous chloride are employed, the result is a drastic reduction in photographic speed. Examples of suitable reduction fogging agents which can be employed in the practice of this invention include hydrazine, phosphonium salts such as tetra(hydroxy methyl) phosphonium chloride, thiourea dioxide, as disclosed in Hillson U.S. Patent 3,062,651, issued Nov. 6, 1962, and Allen et al., U.S. Patent 2,983,609, issued May 9, 1961, reducing agents such as the stannous salts, e.g., stannous chloride, as disclosed in Carroll U.S. Patent 2,487,850 issued Nov. 15, 1939, polyamines such as diethylene triamine as disclosed in Lowe et al., U.S. Patent 2,519,698, issued Aug. 15, 1950, polyamines such as spermine as disclosed in Lowe et al., U.S. Patent 2,521,925, issued Sept. 12, 1950, bis($\beta$-aminoethyl)sulfide and its water soluble salts as disclosed in Lowe et al., U.S. Patent 2,521,926, issued Sept. 12, 1950, and the like.

A gold fogging agent is used in combination with the low concentration of reduction fogging agent to obtain the fogged silver halide grains described herein. The gold fogging agents employed can be any gold salts suitable for fogging, as exemplified by the gold salts disclosed in Waller et al. U.S. Patent 2,399,083, issued Apr. 23, 1946, and Damschroder et al., U.S. Patent 2,642,361, issued June 16, 1953. Specific examples of gold fogging agents are potassium chloroaurite, potassium aurithiocyanate, potassium chloroaurate, auric trichloride, 2-aurosulfobenzothiazole metho chloride, and the like. The concentration of gold fogging agent employed in the practice of this invention is subject to variation but is generally in the range of about 0.001 to about 0.01 millimole per mole of silver halide. Potassium chloroaurate is a preferred gold fogging agent and is most often used at concentrations of less than about 5 mg. per mole of silver halide, and preferably at concentrations in the range of about 0.5 to about 4 milligrams per mole of silver halide. The gold fogging agent often comprises a major portion of the fogging combination with the ratio of gold fogging agent to reduction fogging agent generally being in the range of about 1:3 to about 20:1, often about 2:1 to about 20:1. The silver halide grains are preferably fogged using the reduction fogging agent initially and subsequently using the gold fogging agent. However, the reverse order of agents can be used or the reduction and gold fogging agents can be used simultaneously. The silver halide grains can be fogged prior to coating or they can be coated prior to fogging. The reaction conditions during fogging of the silver halide grains are subject to wide variation although the pH is generally in the range of about 5 to about 7. The pAg is generally in the range of about 7 to about 9 and the temperature is generally in the range of about 40° to about 100° C., most often about 50° to about 70° C. During fogging the silver halide grains can be suspended in a suitable vehicle such as gelatin which is generally employed at a concentration in the range of about 50 to about 200 grams per mole of silver halide.

As already indicated, the fogged silver halide grains described herein are characterized by a rapid loss of fog upon chemical bleaching. The grains will lose at least about 25% and generally at least about 40% of their fog when bleached for ten minutes at 68° F. in a potassium cyanide bleach composition as described herein. This fog loss can be illustrated by coating the silver halide grains as a photographic silver halide emulsion on a support to give a maximum density of at least 1.0 upon processing for six minutes at about 68° F. in Kodak DK-50 developer and comparing the density of such a coating with an identical coating which is processed for six minutes at 68° F. in Kodak DK-50 developer after being bleached for about 10 minutes at 68° F. in the potassium cyanide bleach composition. The maximum density of the unbleached coating will be at least 30% greater, generally at least 60% greater, than the maximum density of the bleached coating. Kodak DK-50 developer is described in the "Handbook of Chemistry and Physics," 30th ed., 1947, Chemical Rubber Publishing Co., Cleveland, Ohio, p. 2558 and has the following composition:

Water, about 125° F. (52° C.)—500 cc.
N-methyl-p-aminophenol sulfate—2.5 grams
Sodium sulfite, desiccated—30.0 grams
Hydroquinone—2.5 grams
Sodium metaborate—10.0 grams
Potassium bromide—0.5
Water to make 1.0 liter.

The direct-positive photographic silver halide emulsions of this invention contain a compound which accepts electrons. Suitable electron accepting compounds including the photoelectron accepting compounds or desensitizing dyes used in photographic reversal systems. Compounds of this type include the known desensitizers which trap electrons, as disclosed in British Patent 723,019, published Feb. 2, 1955. The electron acceptors which gave particular good results in the practice of this invention can be characterized in terms of their polarographic half-wave potentials, i.e., their oxidation reduction potentials determined by polarography. Cathodic measurements can be made with a $1\times10^{-4}$ molar solution of the electron acceptor in a solvent, for example, methanol which is 0.05 molar in lithium chloride using a dropping mercury electrode with the polarographic halfwave potential for the most positive cathodic wave being designated $E_c$. Anodic measurements can be made with $1\times10^{-4}$ molar aqueous solvent solution, for example methanolic solutions of the electron acceptor which are 0.05 molar in sodium acetate and 0.005 molar in acetic acid using a carbon paste of pyrolytic graphite electrode, with the voltametric half peak potential for the most negative anodic response being designated $E_a$. In each measurement, the reference electrode can be aqueous silver-silver chloride (saturated potassium chloride) electrode at 20° C. Electrochemical measurements of this type are known in the art and are described in New Instrumental Methods in Electrochemistry, by Delahay, Interscience Publishers, New York, N.Y., 1954; Polarography, by Kolthoff and Lingane, 2nd ed., Interscience Publishers, New York, N.Y., 1952; Analytical Chemistry, 36, 2426 (1964) by Elving; and Analytical Chemistry, 30, 1576 (1958) by Adams. Plus and minus signs are according to IUPAC (International Union of Pure and Applied Chemistry) Stockholm Convention 1953. Compounds which can be employed as electron acceptors in the practice of this invention include organic compounds having an anodic polarographic halfwave potential ($E_a$) and a cathodic polarographic potential ($E_c$) which when added together give a positive sum. Preferably, such compounds also spectrally sensitize photographc silver halide emulsions to radiation having a wavelength of at least about 480 mμ and generally spectrally sensitize such emulsions in the range of about 480 to about 800 mμ. Advantageously, these compounds provide spectral sensitization such that the ratio of minus blue relative speed to blue relative speed is greater than 7 and preferably greater than 10 when exposed to a tungsten light source through Wratten No. 16 and No. 35 plus 38A filters respectively, and can be termed "spectral sensitizing electron acceptors."

An especially useful class of electron accepting compounds which can be used in the direct-positive photographic silver halide emulsions of this invention are cyanine dyes, particularly imidazoquinoxaline dyes, such as those described in Brooker et al., Belgian Patent 660,253, published Mar. 15, 1965. Very good results are obtained with cyanine dyes containing an indole nucleus aromatically substituted in the 2 position, i.e., a cyanine dye containing a 2-aromatically substituted indole nucleus. One useful class of spectral sensitizing, electron acceptors are the bis-(1-alkyl-2-phenylindole-3)trimethine cyanines described by Coenen et al., U.S. Patent 2,930,694, issued Mar. 29, 1960. Another useful class of dimethine cyanine dyes of this type is described in British Patent 970,601.

Still another class of useful spectral sensitizing electron acceptors are the cyanine and merocyanine dyes in which at least one nucleus and preferably two nuclei, contain desensitizing substituents, such as $NO_2$, e.g., 3,3'-diethyl-6,6'-dinitrothiacarbocyanine chloride, as shown in British Patent 723,019.

The compounds which accept electrons in the direct-positive photographic silver halide emulsions of this invention can be employed in widely varying concentrations. However, such compounds are preferably employed at concentrations in the range of about 100 milligrams to about 2 grams of electron acceptor per mole of silver halide. Specific examples of suitable electron acceptors include the following:

(1) 1,1-Dimethyl-2,2'-diphenyl-3,3'-indolocarbocyanine bromide

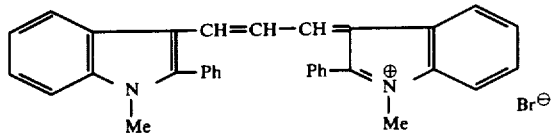

(2)
2,2'-Di-p-methoxyphenyl-1,1'-dimethyl-3,3'-indolocarbocyanine bromide

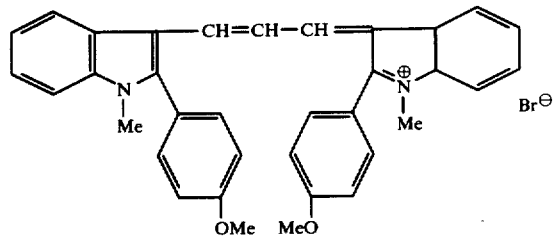

(3)
1,1'-Dimethyl-2,2',8-triphenyl-3,3'-indolocarbocyanine perchlorate

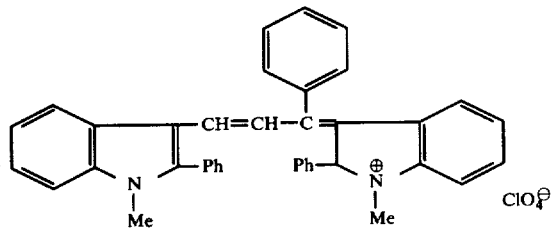

(4)
1,1',3,3'-Tetraethylimidazo[4,5-b]quinoxalinocarbocyanine chloride

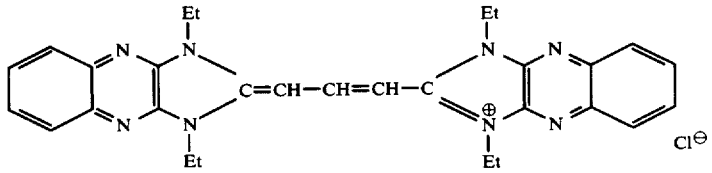

Additional examples include, phenosafranine, pinacryptol yellow, 5-m-nitrobenzylidenerhodanine, 3-ethyl-5-m-nitrobenzylidenerhodanine, 3-ethyl-5-(2,4-dinitrobenzylidene)-rhodanine, 5-o-nitrobenzylidene-3-phenylrhodanine, 1',3-diethyl-6-nitrothia-2'-cyanine iodide, 4-nitro-6-chlorobenzotriazole, 3,3'-diethyl-6,6'-dinitro-9-phenylthiacarbocyanine iodide, 2-(p-dimethylaminophenyliminomethyl)benzothiazole ethoethyl sulfate, Crystal violet, 3,3'-diethyl-6,6'-dinitrothiacarbocyanine ethyl sulfate, 1',3-diethyl-6-nitrothia-2'-cyanine iodide, 1,3-diamino-5-methylphenazinium chloride, 4-nitro-6-chlorobenzotriazole, 3,3'-di-p-nitrobenzylthiacarbocyanine bromide, 3,3'-di-p-nitrophenylthiacarbocyanine iodide, 3,3'-di-o-nitrophenylthiacarbocyanine perchlorate, 3,3'-dimethyl-9-trifluoromethylthiacarbocyanine iodide, 9-(2,4-dinitrophenylmercapto)-3,3'-diethylthiacarbocyanine iodide, bis(4,6-diphenylpyryl-2)trimethincyanine perchlorate, anhydro-2-p-dimethylaminophenyliminomethyl-6-nitro-3-(4-sulfobutyl)benzothiazolium hydroxide, 1-(2-benzothiazolyl)-2-(p-dimethylaminostyryl)-4,6-diphenylpyridinium iodide, 1,3-diethyl-5-[1,3-neopentylene-6-(1,3,3-trimethyl-2-indolinylidene)-2,4-hexadienylidene]-2-thiobarbituric acid, 2,3,5-triphenyl-2H-tetrazolium chloride, 2-(4-iodophenyl)-3-(4-nitrophenyl)-5-phenyltetrazolium chloride, 1-methyl-8-nitroquinolinium methyl sulfate, 3,6-bis[4-(3-ethyl-2-benzothiazolinylidene)-2-butenylidene]-1,2,4,5-cyclohexanetetrone and the like.

The silver halides employed in the preparation of the photographic compositions described herein include any of the photographic silver halides as exemplified by silver bromide, silver iodide, silver chloride, silver chlorobromide, silver bromoiodide, silver chlorobromide, and the like. Silver halide grains having an average grain size less than about one micron, preferably less than about 0.5 micron, give particularly good results. The silver halide grains can be any suitable shape such as cubic or octahedral and preferably have a rather uniform diameter frequency distribution. For example, at least 95% by weight, of the photographic silver halide grains can have a diameter which is within about 40%, preferably within about 30% of the mean grain diameter. Mean grain diameter, i.e., average grain size, can be determined using conventional methods, e.g., such as by projective area as shown in an article by Trivelli and Smith entitled "Empirical Relations Between Sensitometric and Size-Frequency Characteristics in Photographic Emulsion Series" in The Photographic Journal, vol. LXXIX, 1939, pp. 330–338. The fogged silver halide grains in the direct-positive photographic emulsions of this invention produce a density of at least 0.5 when developed without exposure for five minutes at 68° F. in Kodak DK-50 developer when such an emulsion is coated at a coverage of 50 to about 500 mg. of silver per square foot of support. The preferred photographic silver halide emulsions comprise at least 50 mole percent bromide, the most preferred emulsions being silver bromoiodide emulsions, particularly those containing less than about ten mole percent iodide. The photographic silver halides can be coated at silver coverages in the range of about 50 to about 500 milligrams of silver per square foot of support.

Various colloids can be used as vehicles or binding agents in the direct-positive photographic materials of this invention. Satisfactory colloids which can be used for this purpose include any of the hydrophilic colloids generally employed in the photographic field, including, for example, gelatin, collidal albumin, polysaccharides, cellulose derivatives, synthetic resins such as polyvinyl compounds, including polyvinyl alcohol derivatives, acrylamide polymers and the like. In addition to the hydrophilic colloids, the vehicle or binding agent can contain dispersed polymerized vinyl compounds, particularly those which increase the dimensional stability of photographic materials. Suitable compounds of this type include water-insoluble polymers of alkyl acrylates or methacrylates, acrylic acid, sulfoalkyl acrylates or methacrylates, and the like.

The photographic compositions described herein can be coated on a wide variety of supports in preparing photographic elements. The photographic silver halide emulsions can be coated on one or both sides of the support which is preferably transparent and/or flexible. Typical supports are cellulose nitrate film, cellulose acetate film, polyvinyl acetal film, polystyrene film, polyethylene terephthalate film and other polyester film as well as glass, paper, metal, wood and the like. Supports such as paper which are coated with $\alpha$-olefin polymers, particularly polymers of $\alpha$-olefins containing two or more carbon atoms, as exemplified by polyethylene, polypropylene, ethylenebutene copolymers, and the like, give good results.

The photographic silver halide emulsion and other layers present in the photographic elements made according to this invention can be hardened with any suitable hardener, including aldehyde hardeners such as formaldehyde and mucochloric acid, aziridine hardeners, hardeners which are derivatives of dioxane, oxypolysaccharides such as oxystarch or oxy plant gums, and the like.

The photographic silver halide emulsion layers can contain additional additives, particularly those known to be beneficial in photographic emulsions, including, for example, lubricating materials, stabilizers, speed increasing materials, absorbing dyes, plasticizers, and the like. These photographic emulsions can also contain spectral sensitizing dyes in addition to the electron accepting compounds which can spectrally sensitize in some cases. Suitable spectral sensitizers include the cyanines, merocyanines, complex(trinuclear)cyanines, complex(trinuclear)merocyanines, styryls and hemicyanines. Furthermore, these emulsions can contain color forming couplers or can be developed in solutions containing couplers or other color generating materials. The color forming couplers can be incorporated into the direct positive photographic silver halide emulsion using any suitable technique, e.g., techniques of the type shown in Jelley et al., U.S. Patent 2,322,027, issued June 15, 1943; Fierke et al., U.S. Patent 2,801,171, issued July 30, 1957; and Fischer U.S. Patents 1,055,155 and 1,102,028, issued Mar. 4, 1913 and June 30, 1914, respectively, and Wilmanns U.S. Patent 2,186,849, issued Jan. 9, 1940. They can also be developed using incorporated developers such as polyhydroxybenzenes, aminophenols, 3-pyrazolidones, and the like.

It is sometimes advantageous to include surface active agents or compatible mixtures of such agents in the preparation of the photographic materials described herein. Suitable agents of this type include the nonionic, ionic and amphoteric types, as exemplified by polyoxyalkylene derivatives, amphoteric amino acid dispersing agents, including sulfobetaines, and the like. Such surface active agents are described in U.S. Patent 2,600,831, issued June 17, 1952; U.S. Patent 2,271,622, issued Feb. 3, 1942; U.S. Patent 2,271,623, issued Feb. 3, 1942; U.S. Patent 2,275,727, issued Mar. 10, 1942; U.S. Patent 2,787,604, issued Apr. 2, 1957; U.S. Patent 2,816,920 issued Dec. 17, 1957; U.S. Patent 2,739,891, issued Mar. 27, 1956 and Belgian Patent 652,862.

This invention can be further illustrated by the following examples of preferred embodiments thereof although it will be understood that these examples are included merely for purposes of illustration and are not intended to limit the scope of the invention unless otherwise specifically indicated.

EXAMPLE 1

The direct-positive photographic silver halide emulsions of this invention comprise silver halide grains characterized by a rapid loss of fog upon chemical bleaching. Futhermore, low concentrations of reduction and gold fogging agents are used in order to obtain such silver halide grains. To illustrate these features, a medium grain photographic gelatino silver bromoiodide emulsion containing approximately one mole percent iodide is prepared using the procedure described for Emulsion No. 10 in the Trivelli and Smith article entitled, "Empirical Relations Between Sensitometric and Size-Frequency Characteristics in Photographic Emulsion Series," published in The Photographic Journal, vol. LXXIX, May 1939 (pp. 330–338), except that the emulsion is not chemically sensitized, i.e., the second ripening is omitted. The average grain size of this emulsion is about 0.4 micron. The emulsion is divided into several portions and each portion is reduction and gold fogged by simultaneously adding a reducing agent with a gold salt and heating the emulsion at 65° C. for 50 minutes using the fogging agent concentrations listed in the following Table 1. 1.5 g. of an electron accepting compound (pinacryptal yellow) per mole of silver halide is added to each portion of the emulsion. A sample of each portion of the emulsion is coated on conventional cellulose acetate film support at coverages of 230 mg. of silver and 745 mg. of gelatin per square foot of support. A sample of each coating is exposed on an Eastman Ib sensitometer, developed for 6 minutes in Kodak DK-50 developer, fixed, washed and dried. The maximum density, photographic speed at a given density below maximum density, and gamma are determined using the same procedure for each coating of the emulsion portions. The results are as follows:

TABLE 1

| | Reducing Agent | | Gold Fogging Agent | | | | |
|---|---|---|---|---|---|---|---|
| Coating | Compound | Mg./mole Agr | Compound | Mg./mole Agr | $D_{max.}$ | Rel. Speed | $\gamma$ |
| 1 | Thiourea dioxide | 0.4 | Potassium chloroaurate. | 2.0 | 1.74 | 11,000 | 2.38 |
| 2 | " | 0.75 | " | 7.5 | 1.80 | 316 | 1.80 |
| 3 | " | 1.5 | " | 15.0 | 1.82 | 145 | 1.78 |
| 4 | Stannous chloride | 1.5 | Auric trichloride | 15.0 | 1.80 | 100 | 1.45 |

It can be seen from the above results the reduction fogging agent and the gold fogging agent combination is employed at low concentrations (Coating No. 1) in order to obtain the direct-positive photographic silver halide emulsions of this invention which exhibit a truly phenomenal increased photographic speed. When the above procedure is repeated using stannous chloride with auric trichloride at the low concentrations given for Coating No. 1 a comparable speed is obtained.

The rapid loss of fog upon chemical bleaching of the fogged silver halide grains disclosed herein is illustrated by bleaching a sample of each of the above coated emulsion portions before development in a chemical bleach having the following composition:

Potassium cyanide—50 mg.
Acetic acid (glacial)—3.47 cc.
Sodium acetate—11.49 g.
Potassium bromide—119 mg.
Water to 1 liter.

The films are bleached for ten minutes at 68° F. in the above bleach without agitation. Coatings are then washed in running water for ten minutes and allowed to dry at room temperature. The coatings are then developed for 6 minutes in Kodak DK-50 developer fixed, washed and dried in the conventional manner. The results obtained are set forth in the following Table 2.

TABLE 2

| Coating | $D_{max}$ before bleaching | $D_{max}$ after bleaching | Percent Loss in $D_{max.}$ |
|---|---|---|---|
| 1 | 1.74 | 0.88 | 50 |
| 2 | 1.80 | 1.74 | 3.5 |
| 3 | 1.82 | 1.74 | 4.4 |
| 4 | 1.80 | 1.61 | 10 |

Similar results are obtained when the above procedure is repeated with reduction fogging agents such as hydrazine, tetra(hydroxy methyl)phosphonium chloride, triethylene tetramine, and gold fogging agents such as potassium aurithiocyanate and 2-aurosulfobenzothiazole metho chloride.

EXAMPLE 2

As previously indicated, the reduction fogging agent and gold fogging agent can be added in a stepwise manner. Furthermore, an increase in the concentration of reduction fogging agent reduces photographic speed. To illustrate each of these features, a fine grain silver bromoiodide emulsion is prepared according to the procedure described for Emulsion No. 9 in the Trivelli and Smith article referred to in Example 1. The average grain size of the silver halide in the photographic emulsion is about 0.2 micron. The resulting emulsion is split into two portions which are fogged by first adding thiourea dioxide and heating for 60 minutes at 65° C. and then adding potassium chloroaurate and heating the emulsion for 80 minutes at 65° C. with the concentrations of fogging agent listed in the following Table 3. An electron accepting compound (5-m-nitrobenzylidenerhodanine) is incorporated into each portion of the emulsion at a concentration of 0.2 g./mole of silver halide. Each portion of the emulsion is coated on conventional cellulose acetate film support at a coverage of 100 mg. of silver and 350 mg. of gelatin per square foot of support. A sample of each coating is exposed and processed as described in Example 1. The results are as follows:

TABLE 3

| Coating | Thiourea dioxide (mg./mole Agr) | Potassium chloroaurate (mg./mole Agr) | $D_{max.}$ | Rel. Speed | $\gamma$ |
|---|---|---|---|---|---|
| 1 | 0.4 | 2.0 | 1.8 | 2,000 | 8 |
| 2 | 1.5 | 10.0 | 1.8 | 100 | 0.4 |

The photographic speed of Coating No. 2 in the above procedure is comparable to that of a conventional type enlarging paper and is illustrative of the photographic speed exhibited by prior art reduction and gold fogged direct-positive silver halide emulsions. It can be seen from the above table that the photographic emulsions described herein exhibit photographic speeds up to 20 times that of such prior art materials. Furthermore, it has been found that the ratio of reduction fogging agent to gold fogging agent has a significant effect upon the photographic speed of the direct-positive photographic silver halide emulsions disclosed herein. Thus, when the ratio of gold fogging agent to reduction fogging agent in the above procedure is increased to about 25:1, the photographic speed is reduced by over 50%.

EXAMPLE 3

As previously indicated, spectral sensitizing dyes which are not electron acceptors can be incorporated into the direct-positive photographic silver halide emulsions of this invention. To illustrate, a reduction-gold fogged emulsion is prepared as follows: A silver bromoiodide gelatin emulsion containing approximately 2.5 mole percent iodide and having an everage grain size of about 0.2 micron is prepared by adding an aqueous solution of potassium bromide and potassium iodide, and an aqueous solution of silver nitrate, simultaneously to a rapidly agitated aqueous gelatin solution at a temperature of 70° C., over a period of about 35 minutes. The emulsion is chill-set, shredded and washed by leaching with cold water in the conventional manner. The emulsion is reduction gold fogged by first adding 0.2 mg. of thiourea dioxide per mole of silver halide and heating for 60 minutes at 60° C. and then adding 0.4 mg. of potassium chloroaurate per mole of silver halide and heating for 60 minutes at 65° C. 0.2 g. per mole of silver halide of 5-m-nitrobenzylidenerhodanine is added to the fogged emulsion. The emulsion is spectrally sensitized with the sensitizing dyes listed in the following Table 4. Portions of the emulsion are coated on cellulose acetate film support at a coverage of 100 mg. of silver and 400 mg. of gelatin per square foot of support. The coated samples are exposed for 10 seconds on an Eastman Ib sensitometer to light from a tungsten source modulated by a continuous wedge and a Wratten No. 16 filter to demonstrate spectral sensitivity. The film samples are developed for five minutes in Kodak DK-50 developer, fixed, washed and dried in the usual manner. The results are as follows:

TABLE 4

| | | White Light Exposure | | | Wratten No. 16 Filter Exposure (Minus Blue Exposure) | | |
|---|---|---|---|---|---|---|---|
| Sample | Sensitizing Dye (g./mole | $D_{max.}$ | $D_{min.}$ | Rel. Speed | $D_{max.}$ | $D_{min.}$ Speed | Rel. |
| 1 | none | 1.46 | .04 | 363 | 1.4 | 1.34 | <1 |
| 2 | Anhydro-1-ethyl-1'-(4-sulfobutyl)-2,2' cyanine hydroxide (0.2). [(1-ethyl-2-(1H)-naphtho[1,2]thiazolyl-idene)isopropylidene-3-methyl-1-(p-sulfophenyl)-2-pyrazolin-5-one (0.14) Anhydro-1'-ethyl-3-(3-sulfobutyl)-thia-2-cyanine hydroxide (0.7). | 0.98 | 0.2 | 1,070 | .79 | .02 | 513. |

EXAMPLE 4

Color forming couplers can be incorporated into the direct-positive photographic silver halide emulsions described herein. To illustrate, the dyes indicated in the following Table 5 are added to samples of the reduction and gold fogged silver bromoiodide emulsion of Example 3 which contains the electron acceptor 5-m-nitrobenzylidenerhodanine. The emulsion is then digested for ten minutes at 52° C. Coupler dispersions melted at 40° C. are added to the emulsion where indicated in the following Table 5. The emulsions are cooled to 40° C. coated on conventional cellulose acetate film support, chill-set and dried as in Example 3. The film coatings are exposed and processed as indicated in the following table to give reversal images in color.

TABLE 5

| Coating | Dye (g./mole) | Region of sensi tization | Color Forming Coupler | Exposure | Color of Dye Formed by Coupler | Type of Process |
|---|---|---|---|---|---|---|
| 1 | None | Blue | α-benzoyl-3-[α-(2,4-di-amyl-phenoxy)butyramide]-2-methoxyacetanilide | Tungsten source Wratten No. 35+38A filter. | Yellow | A |
| 2 | Anhydro-1'-ethyl-3-(3-sulfobutyl)thia-2'-cyanine hydroxide (0.2)-anhydro-1-ethyl-1'-(4 sulfobutyl)-2,2'-cyanine hydroxide (0.2). | Green | 1-(2,4,6-trichloro-phenyl) 3,3'(2",4"-di-t-amylphenoxy-acet-amido) benzimidazo-5-pyrazolone. | Tungsten source Wratten No. 61+16 filter. | Magenta | A |
| 3 | 3,3'-dimethyl-8,10-di-(m-toloxy)thiacarbo-cyanine bromide (0.2). | Red | 5-[α-(2,4-di-t-amyl-phenoxy)hexanamido]-2-heptafluorobutyramido-phenol. 1-hydroxy-2(α-2,4-di-t-amylphenoxy-n-butyl]naphthamide. | Tungsten source Wratten No. 29 filter. | Cyan | A |
| 4 | 3,3'-dimethyl-8,10-di-(m-toloxy)thiacarbo- | Red | 1-hydroxy-2-[β-(2-acetamido)-phenethyl] | Daylight Quality source Wratten No. 16 filter. | " | B |

TABLE 5-continued

| Coating | Dye (g./mole) | Region of sensitization | Color Forming Coupler | Exposure | Color of Dye Formed by Coupler | Type of Process |
|---|---|---|---|---|---|---|
| | cyanine bromide (0.2). | | naphthalamide. | | | |

A-Reversal color process as described in Graham et II. U.S. Pat. 3,046,129, issued July 24, 1962 in Example (a) (col. 27, lines 25 et seq.) except that black-and-white (MQ) development is omitted and the color development is reduced to 1 minute and done in total darkness until after fixing.
B-Color process for developing cyan dye images as described in Vittum et al., U.S. Pat. 3,002,836 issued Oct. 3, 1961 in Example III (col. 4, lines 45 et seq.) except that black-and-white (MQ) development is omitted.

Thus, by the practice of this invention there is provided direct-positive photographic silver halide emulsions exhibiting excellent photographic speed. Such emulsions can be prepared using gold fogging agents in combination with reduction fogging agents at low concentrations. However, in some applications where the same speed characteristics are not required, other fogging agents can be substituted for the gold fogging agent. Suitable agents of this type include, for example, compounds of metals which are more electropositive than silver, including, e.g., platinum, palladium and other noble metal compounds. Due to their unique photographic speed, the direct-positive photographic silver halide emulsions disclosed herein are particularly useful in a variety of applications in the photographic field. For example, they can be used in lithographic printing plates, particularly those of the type disclosed in U.S. Patent 3,146,104, issued Aug. 25, 1965, color transfer materials, direct reversal color processes, duplicating film, e.g. microfilm, etc. If desired, the silver halide grains can be gold fogged using special processing techniques, for example, a coating of a reduction fogged silver halide emulsion containing an electron accepting conpound can be exposed and bathed in a solution of a gold salt such as gold thiocyanide which can contain a small concentration, for example, less than about 0.5%, of a halogen such as bromide. The coating can then be processed in an alkaline developer such as Kodak DK-50 or Kodak DK-19 developer for 5-10 minutes. Another interesting reversal system involves developing, in a fogging developer, a photographic silver halide emulsion which has been treated with a reduction fogging agent such as stannous chloride. This system involves exposing and developing the aforesaid photographic emulsion in an alkaline fogging developer such as Kodak DK-50 developer to which small concentrations, for example, up to about 0.2 gram per liter, of triethylenetetramine and 1-phenyl-3-pyrazolidone have been added to obtain a reversal image.

The fogged direct-positive photographic silver halide emulsions described herein can also be used in negative azo dye image formation. The art of bleaching an azo dye by chemistry involving the oxidation of metallic silver is well known. In such methods an azo dye in a coating containing a stepwise image of metallic silver is bleached proportional to the silver under strongly acidic conditions giving a reversal image in dye. Bleaching rates are enhanced by accelerators such as 2-hydroxy-3-amino phenazine or anthraquinone-$\beta$-sulfonic acid as shown, for example, at p. 643 of Photographic Chemistry, England language edition, vol. 2 by Pierre Glafkides. This type of bleaching process can employ a very fine grain direct-positive photographic

TABLE 6

| Coating | Dye (g./mole) | Region of sensitization | Color Forming Coupler | Exposure | Color of Dye Formed by Coupler | Type of Process |
|---|---|---|---|---|---|---|
| 1 | None | Blue | $\alpha$-bentoyl-3-[$\alpha$-(2,4-di-amyl. phenoxy)butramide)-2-methoxyacetanilide | Tungsten source Wratten No. 35+38A filter. | Yellow | A |
| 2 | Anhydro-1'-ethyl-3-(3-sulfobutyl)thia-2'-cyanine hydroxide (0.2)+ anhydro-1-ethyl-1'-(4-sulfobutyl)-2,2'-cyanine hydroxide (0.2). | Green | 1-(2,4,6-trichloro-phenyl)-3,3 (2'',4''-di-t-amylphenoxy-acet-amido)benzimidazo-5-pyrazolone. | Tungsten source Wratten No. 61+16 filter. | Magenta | A |
| 3 | 3,3'-dimethyl-8,10-di-(m-toloxy)thiacarbo-cyanine bromide (0.2). | Red | 5-[$\alpha$-(2,4-di-t-amyl-phenoxy)hexanamido]-2-heptafluorobutyramido-phenol. 1-hydroxy-2'$\alpha$-(2,4-di-t-amylphenoxy-n-butyl-t-naphthamide. | Tungsten source Wratten No. 29 filter. | Cyan | A |
| 4 | 3,3'-dimethyl-8,10,dt-(m-toloxy)thiacarbo-cyanine bromide (0.2). | Red | 1-hydroxy-2-[$\beta$-(2-acetoamido)-phenethyl)-naphthalamide | Daylight Quality source Wratten No. 16 filter. | " | B |

A-Reversal color process as described in Graham et al. U.S. Patent 3,046,129, issued July 24, 1962 in Example (a) (col. 27, lines 25 et seq.) except that black-and-white (MQ) development is omitted and the color development is reduced to 1 minute and done in total darkness until after fixing.
B-Color process for developing cyan dye images as described in Vittum et al. U.S. Patent 3,002,836 issued Oct. 3, 1961 in Example III (col. 4, lines 45 et seq) except that black-and-white (MQ) development is omitted.

As shown herein, color forming couplers can be incorporated into the direct-positive photographic silver halide emulsions of this invention. It has been found that the incorporation of a color forming coupler or coupler solvent in the emulsion significantly improves the quality of the reversal obtained in black and white elonhydroquinone type developers. There is obtained an increase in contrast and a lower minimum density using this type developer with such emulsions.

The fogged, direct-positive photographic silver halide emulsions can also be used in color diffusion transfer systems in combination with dye developers. Photographic developers which contain a dye moiety can, of course, be synthesized. Upon applying an alkaline solution to an imagewise exposed negative developing silver halide emulsion element containing one of these dye developers, the dye developer becomes immobilized within the element where development occurs, that is, in the exosed areas. When an alkaline treated sample of this material is brought into contact with a receiver sheet, there is obtained a positive transfer print composed of transferred dye-developer and a negative print composed of nontransferred dye developer when the negative silver image is bleached. Dye developer coatings made with a reversal emulsion of the type disclosed herein will develop to yield a positive silver image. Therefore, an alkaline treated sample of this material brought in contact with a receiver will yield a negative dye transfer print composed of transferred dye-developer and a positive print composed of non-transferred dye-developer when the positive silver image is bleached.

The fogged, direct-positive photographic silver halide emulsions of this invention can also be used in reversal chemical transfer systems. The chemical transfer system is often used for making positive copies from positive originals and is very popular since stable right-reading images are readily obtained. The negative is exposed in a normal manner, then passed through a solvent developer in contact with a nucleated receiver. The exposed negative silver is developed, while the unexposed silver halide dissolves and diffuses to the receiver sheet where it is deposited on the nuclei and developed. The chemical transfer print can be obtained in a short time since no additional processing steps are necessary. The fogged, direct-positive photographic silver halide emulsions of this invention, upon exposure to a negative image, followed by development, give a negative silver image in the emulsion layer. In the presence of a solvent developer, the exposed silver halide which has not developed, migrates to the nucleated receiver where it is deposited as a positive image. The emulsions of this invention can be used in chemical transfer processes employed to make a chemical transfer print by either the one-sheet system, in which the emulsion is coated on the same support as the receiver layer, or by the two-sheet system, in which the emulsion and receiver layers are coated on separate supports.

The direct-positive photographic silver halide emulsions of this invention can also be processed in the presence of ammonia vapors or other gaseous compounds of the type disclosed in U.S. Patent 3,158,481, issued Nov. 24, 1964; U.S. Patent 3,144,334, issued Aug. 11, 1964, and British Patent 973,965, published Nov. 4, 1964. The developing agent can be incorporated into the emulsion coating or in a separate sheet. Ammonia or another gaseous compound which is used to activate the coating can be incorporated in a separate layer of the element containing the emulsion. The ammonia or other activator can be in any suitable form, for example, in the form of an ammonia polymer. Such activating materials can also be incorporated in a sheet separate from the element containing the emulsion and activated by heat. Processing with ammonia or other activators is of special interest in the document copying field where the emulsion is coated on paper or as a film duplicating material where the emulsion is coated on film.

Although the invention has been described in considerable detail with reference to certain preferred embodiments thereof, it will be understood that variations and modifications can be effected without departing from the spirit and scope of the invention as described hereinabove and as defined in the appended claims.

I claim:

1. A direct-positive, photographic emulsion which comprises fogged silver halide grains and an organic desensitizer which has an anodic polarographic half-wave potential and a cathodic half-wave potential which, when added together, give a positive sum, said grains being such that a test portion thereof, when coated as a photographic silver halide emulsion on a support to give a maximum density of at least about 1 upon processing for 6 minutes at about 68° F. in Kodak DK-50 developer, has a maximum density which is at least about 30% greater than the maximum density of an identical coated test portion which is processed for 6 minutes at about 68° F. in Kodak DK-50 developer after being bleached for about 10 minutes at about 68° F. in a bleach composition of:

Potassium cyanide—50 mg.
Acetic acid (glacial)—3.47 cc.
Sodium acetate—11.49 g.
Potassium bromide—119 mg.
Water to 1 liter.

2. The photographic emulsion of claim 1 in which the grains are fogged with about 0.0005 to about 0.06 milliequivalent per mole of silver halide of a reduction fogging agent and about 0.001 to about 0.01 millimole per mole of silver halide of a gold fogging agent.

3. The photographic emulsion of claim 1 in which the silver halide comprises at least 50 mole percent bromide and the silver halide grains are fogged with about 0.0005 to about 0.06 milliequivalent per mole of silver halide of a reduction fogging agent and about 0.001 to about 0.01 millimole per mole of silver halide of a gold fogging agent, the ratio of gold fogging agent to reduction fogging agent being in the range of about 1:3 to about 20:1.

4. The photographic emulsion of claim 1 in which the silver halide grains have an average grain size less than about 1 micron and are fogged with a reduction fogging agent and a gold fogging agent.

5. The photographic emulsion of claim 1 in which the silver halide grains have an average grain size of less than about 1 micron, are fogged with a reduction fogging agent and a gold fogging agent and said desensitizer is an organic compound which spectrally sensitizes in the range of about 480 to about 800 mμ.

6. The photographic emulsion of claim 2 in which said desensitizer is a cyanine dye.

7. The photographic emulsion of claim 1 which contains a spectral sensitizing dye in addition to said desensitizer.

8. The photographic emulsion of claim 2 in which said desensitizer is an imidazoquinoxaline dye.

9. The photographic emulsion of claim 6 in which the silver halide is silver bromoiodide comprising at least 50 mole percent bromide and less than about 10 mole percent iodide.

10. A photographic element comprising a support and at least one photographic silver halide layer which comprises fogged silver halide grains and an organic desensitizer which has an anodic polarographic half-wave potential and a cathodic half-wave potential which, when added together, give a positive sum, said grains being such that a test portion thereof, when coated as a photographic silver halide emulsion on a support to give a maximum density of at least about 1 upon processing for 6 minutes at about 68° F. in Kodak DK-50 developer, has a maximum density which is at least about 30% greater than the maximum density of an identical coated test portion which is processed for 6 minutes at about 68° F. in Kodak DK-50 developer after being bleached for about 10 minutes at about 68° F. in a bleach composition of:

Potassium cyanide—50 mg.
Acetic acid (glacial)—3.47 cc.
Sodium acetate—11.49 g.
Potassium bromide—119 mg.
Distilled water to 1 liter.

11. The photographic element of claim 10 in which the silver halide grains are fogged with a reduction fogging agent and a gold fogging agent.

12. The photographic element of claim 11 in which the concentration of gold fogging agent is in the range of about 0.001 to about 0.01 millimole per mole of silver halide.

13. The photographic element of claim 11 in which the silver halide comprises at least 50 mole percent bromide and the silver halide grains are fogged with about 0.0005 to about 0.06 milliequivalent per mole of silver halide of the reduction fogging agent and about 0.001 to about 0.01 millimole per mole of silver halide of the gold fogging agent.

14. The photographic element of claim 10 in which the silver halide is silver bromoiodide comprising at least 50 mole percent bromide and up to about 10 mole percent of iodide.

15. The photographic element of claim 11 in which the photographic silver halide layer is a gelatin photographic silver halide layer.

16. The photographic element of claim 10 in which the silver halide grains are fogged with a reduction fogging agent and a gold fogging agent, the photographic silver halide layer is a gelatin photographic silver halide layer and the silver halide grains have an average grain size up to about 1 micron.

17. The photographic element of claim 10 in which the silver halide grains are fogged with a reduction fogging agent and a gold fogging agent and said desensitizer is an organic compound which spectrally sensitizes in the range of about 480 to about 800 mμ and comprises, contiguous to the silver halide grains, a color-forming coupler.

18. The photographic element of claim 10 in which the silver halide grains are fogged with about 0.0005 to about 0.06 milliequivalent per mole of silver halide or a reduction fogging agent and about 0.001 to about 0.01 millimole per mole of silver halide of a gold fogging agent, the ratio of gold fogging agent to reduction fogging agent tbeing in the range of 1:3 to about 20:1, the silver halide comprises at least about 50 mole percent bromide and said desensitizer is a cyanine dye.

19. The photographic element of claim 18 in which the cyanine dye is an imidazoquinoxaline dye.

20. The photographic element of claim 18 in which the silver halide is a silver bromoiodide which comprises at least 50 mole percent bromine and up to about 10 mole percent iodine.

21. The photographic element of claim 18 in which the reduction fogging agent is thiourea dioxide and the gold fogging agent is potassium chloroaurate.

22. The photographic element of claim 18 in which the reduction fogging agent is thiourea dioxide, the gold fogging agent is potassium chloroaurate and the silver halide is silver bromoiodide which comprises at least 50 mole percent bromine and up to about 10 mole percent iodine.

23. The process which comprises contacting silver halide grains with about 0.0005 to about 0.06 milliequivalent per mole of silver halide of a reduction fogging agent and about 0.001 to about 0.001 millimole per mole of silver halide of a gold fogging agent at a temperature in the range of about 40° to about 100° C., the ratio of gold fogging agent to reduction fogging agent being in the range of about 1:3 to about 20:1.

24. The process of claim 23 in which the silver halide comprises at least 50 mole percent bromide.

25. The process of claim 23 in which the silver halide has an average grain size up to about 1 micron.

26. The process of claim 23 in which the silver halide grains are contacted with the reduction fogging agent and are subsequently contacted with the gold fogging agent.

27. The process of claim 23 in which the reduction fogging agent is thiourea dioxide and the gold fogging agent is potassium chloroaurate.

28. The process of claim 23 comprising adding a desensitizer compound to the silver halide grains after they have been contacted with the reduction and gold fogging agents.

29. Fogged, photographic silver halide grains being such that a test portion thereof, when coated as a photographic silver halide emulsion on a support to give a maximum density of at least about 1 upon processing for 6 minutes at about 68° F. in Kodak DK-50 developer, has a maximum density which is at least about 30% greater than the maximum density of an identical coated test portion which is processed for 6 minutes at about 68° F. in Kodak DK-50 developer after being bleached for about 10 minutes at about 68° F. in a bleach composition of:

Potasssium cyanide—50 mg.
Acetic acid (glacial)—3.47 cc.
Sodium acetate—11.49 g.
Potassium bromide—119 mg.
Water to 1 liter.

30. The photographic silver halide grains of claim 29 fogged with about 0.0005 to about 0.06 milliequivalent per mole of silver halide of a reduction fogging agent and about 0.001 to about 0.01 millimole per mole of silver halide of a gold fogging agent.

31. The photographic silver halide grains of claim 29 in which the silver halide comprises at least 50 mole percent bromide and the grains are fogged with about 0.0005 to about 0.06 milliequivalent per mole of silver halide of a reduction fogging agent and about 0.001 to about 0.01 millimole per mole of silver halide of a gold fogging agent, the ratio of gold fogging agent to reduction fogging agent being in the range of about 1:3 to about 20:1.

32. The photographic silver halide grains of claim 31 having an average grain size less than about one micron.

33. The photographic silver halide grains of claim 29 wherein said grains are fogged with about 0.0005 to about 0.06 milliequivalent per mole of silver halide of a reduction fogging agent and about 0.001 to about 0.01 millimole per mole of silver halide of a gold fogging agent and having an organic desensitizer compound adjacent said grains which has an anodic polarographic half-wave potential and a cathodic half-wave potential which, when added together, give a positive sum.

34. A direct-positive, photographic emulsion which comprises fogged silver halide grains and a desensitizer which has an anodic polarographic half-wave potential and a cathodic half-wave potential which, when added together, give a positive sum, said grains being such that a test portion thereof, when coated as a photographic silver halide emulsion on a support to give a maximum density of at least about 1 upon processing for 6 minutes at about 68° F. in Kodak DK-50 developer, has a maximum density which is at least about 30% greater than the maximum density of an identical coated test portion which is processed for 6 minutes at about 68° F. in Kodak DK-50 developer after being bleached for about 10 minutes at about 68° F. in a bleach composition of:

Potassium cyanide—50 mg.
Acetic acid (glacial)—3.47 cc.
Sodium acetate—11.49 g.
Potassium bromide—119 mg.
Water to 1 liter.

*35. The photographic emulsion of claim 1 in which said grains are such that a test portion thereof, when coated as a photographic silver halide emulsion on a support to give a maximum density of at least about 1 upon processing for 6 minutes at about 68° F. in Kodak DK-50 developer has a maximum density which is at least about 60% greater than the maximum density of an identical coated test portion which is processed for 6 minutes at about 68° F. in Kodak DK-50 developer after being bleached for about 10 minutes at about 68° F. in a bleach composition of:*

*Potassium cyanide—50 mg.*
*Acetic acid (glacial)—3.47 cc.*
*Sodium acetate—11.49 g.*
*Potassium bromide—119 mg.*
*Water to 1 liter.*

*36. The photographic element of claim 10 in which said grains are such that a test portion thereof, when coated as a photographic silver halide emulsion on a support to give a maximum density of at least about 1 upon processing for 6 minutes at about 68° F. in Kodak DK-50 developer, has a maximum density which is at least about 60% greater than the maximum density of an identical coated test portion which is processed for 6 minutes at about 68° F. in Kodak DK-50 developer after being bleached for about 10 minutes at about 68° F. in a bleach composition of:*

*Potassium cyanide—50 mg.*
*Acetic acid (glacial)—3.47 cc.*
*Sodium acetate—11.49 g.*
*Potassium bromide—119 mg.*
*Water to 1 liter.*

*37. The fogged photographic silver halide grains of claim 29 in which said grains are such that a test portion thereof, when coated as a photographic silver halide emulsion on a support to give a maximum density of at least about 1 upon processing for 6 minutes at about 68° F. in Kodak DK-50 developer, has a maximum density which is at least about 60% greater than the maximum density of an identical coated test portion which is processed for 6 minutes at about 68° F. in Kodak DK-50 developer after being bleached for about 10 minutes at about 68° F. in a bleach composition of:*

*Potassium cyanide—50 mg.*
*Acetic acid (glacial)—3.47 cc.*
*Sodium acetate—11.49 g.*
*Potassium bromide—119 mg.*
*Water to 1 liter.*

*38. The photographic emulsion of claim 34 in which said grains are such that a test portion thereof, when coated as a photographic silver halide emulsion on a support to give a maximum density of at least about 1 upon processing for 6 minutes at about 68° F. in Kodak DK-60 developer, has a maximum density which is at least about 60% greater than the maximum density of an identical coated test portion which is processed for 6 minutes at about 68° F. in Kodak DK-50 developer after being bleached for about 10 minutes at about 68° F. in a bleach composition of:*

*Potassium cyanide—50 mg.*
*Acetic acid (glacial)—3.47 cc.*
*Sodium acetate—11.49 g.*
*Potassium bromide—119 mg.*
*Water to 1 liter.*

*39. A direct-positive photographic emulsion which comprises an electron acceptor in combination with fogged silver halide grains wherein at least 95% by weight or by number of the silver halide grains are of a size which is within about 40% of the mean grain size, said grains being such that a test portion thereof, when coated as a photographic silver halide emulsion on a support to give a maximum density of at least about 1 upon processing for 6 minutes at about 68° F. in Kodak DK-50 developer, has a maximum density which is at least about 30% greater than the maximum density of an identical coated test portion which is processed for 6 minutes at about 68° F. in Kodak DK-50 developer after being bleached for about 10 minutes at about 68° F. in a bleach composition of:*

*Potassium cyanide—50 mg.*
*Acetic acid (glacial)—3.47 cc.*
*Sodium acetate—11.49 g.*
*Potassium bromide—119 mg.*
*Water to 1 liter.*

*40. The photographic emulsion of claim 39 in which said grains are such that a test portion thereof, when coated as a photographic silver halide emulsion on a support to give a maximum density of at least about 1 upon processing for 6 minutes at about 68° F. in Kodak DK-50 developer, has a maximum density which is at least about 60% greater than the maximum density of an identical coated test portion which is processed for 6 minutes at about 68° F. in Kodak DK-50 developer after being bleached for about 10 minutes at about 68° F. in a bleach composition of:*

*Potassium cyanide—50 mg.*
*Acetic acid (glacial)—3.47 cc.*
*Sodium acetate—11.49 g.*
*Potassium bromide—119 mg.*
*Water to 1 liter.*

*41. The photographic emulsion of claim 39 wherein said silver halide grains are reduction and gold fogged.*

*42. The photographic emulsion of claim 39 wherein the slver halide is silver bromoiodide comprising at least 50 mole percent bromide and up to about 10 mole percent iodide.*

*43. The photographic emulsion of claim 39 wherein said silver halide grains are cubic.*

*44. The photographic emulsion of claim 39 wherein said silver halide emulsion contains a spectral sensitizing dye.*

*45. The photographic emulsion of claim 39 wherein said silver halide emulsion contains a desensitizer which has an anodic polarographic half-wave potential and a cathodic half-wave potential which, when added together, give a positive sum.*

*46. The photographic emulsion of claim 39 wherein said slver halide emulsion contains a color-forming coupler.*

*47. A direct-positive photographic element comprising a support and at least one photographic silver halide emulsion layer which comprises an electron acceptor compound and reduction and gold fogged, cubic silver halide grains in which said silver halide is silver bromoiodide comprising at least 50 mole percent bromide and up to about 10 mole percent iodide and at least 95% by weight or by number of the silver halide grains being of a size which is within about 40% of the mean grain size, said grains being such that a test portion thereof, when coated as a photographic silver halide emulsion on a support to give a maximum density of at least about 1 upon processing for 6 minutes at about 68° F. in Kodak DK-50 developer, has a maximum density which is at least about 60% greater than the maximum density of an identical coated test portion which is processed for 6 minutes at about 68° F. in Kodak DK-50 developer after being bleached for about 10 minutes at about 68° F. in a bleach composition of:*

*Potassium cyanide—50 mg.*
*Acetic acid (glacial)—3.47 cc.*
*Sodium acetate—11.49 g.*
*Poassium bromide—119 mg.*
*Water to 1 liter.*

*48. A direct-positive photographic element according to claim 47 wherein said silver halide emulsion contains a dye-forming coupler and a spectral sensitizing dye.*

*49. A direct-positive photographic element according to claim 47 wherein said silver halide emulsion contains an organic desensitizer which has an anodic polarographic half-wave potential and a cathodic half-wave potential which, when added together, give a positive sum.*

* * * * *